(12) United States Patent
Gerdes et al.

(10) Patent No.: US 6,281,209 B1
(45) Date of Patent: *Aug. 28, 2001

(54) FUNGICIDAL ALKOXIMINOMETHYLDIOXAZINE DERIVATIVES

(75) Inventors: Peter Gerdes, Aachen; Herbert Gayer, Monheim; Bernd-Wieland Krüger, Bergisch Gladbach; Ulrich Heinemann, Leichlingen; Bernd Gallenkamp, Wuppertal; Ralf Tiemann, Leverkusen; Stefan Dutzmann; Karl-Heinz Kuck, both of Langenfeld; Klaus Stenzel, Düsseldorf, all of (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/380,914

(22) PCT Filed: Mar. 2, 1998

(86) PCT No.: PCT/EP98/01165

§ 371 Date: Sep. 10, 1999

§ 102(e) Date: Sep. 10, 1999

(87) PCT Pub. No.: WO98/40365

PCT Pub. Date: Sep. 17, 1998

(30) Foreign Application Priority Data

Mar. 13, 1997 (DE) .............................................. 197 10 355

(51) Int. Cl.[7] .................... A61K 31/535; C07D 265/00
(52) U.S. Cl. ............................................ 514/229.2; 544/65
(58) Field of Search ............................. 544/65; 514/229.2

(56) References Cited

FOREIGN PATENT DOCUMENTS 080225    11/1982  (EP) .

95/04728  * 2/1995  (WO) .

OTHER PUBLICATIONS

J. Med. Chem., (Month Unavailable), 1981, vol. 24, pp. 525–532, Balsamo et al, "Structure–Activity Relationship in Cinnamamides. 3.[1] Synthesis and Anticonvulsant Activity Evaluation of Some Derivatives of (E)– and (Z)–m–(Trifluoromethyl)cinnamamide".
J. Chem. Soc., (Month Unavailable), 1963, pp. 4210–4218, Padmanathan et al, "Unsaturated Systems. Part IV. The ortho–Claisen Rearrangement of α–and γ–Aryloxy–β–methylcrotonates and α–Phenoxy–γ–methylcrotonate".
J. Chem. Eng. Data, vol. 10, (Month Unavailable), 1965, pp. 72–73, Wiley et al, "Cis–Trans Isomers of Methyl Substituted Fluorocinnamic and 5–(o–, m–, and p–Fluorophenyl)pentadienoic Acids".
Chem. Ber., (Month Unavailable), 1907, Diels et al, "Über die Kondensation von Oxalester mit Dimethylketol".

* cited by examiner

Primary Examiner—Mukund J. Shah
Assistant Examiner—Hong Liu
(74) Attorney, Agent, or Firm—Joseph C. Gil; Jackie Ann Zurcher

(57) ABSTRACT

The invention relates to alkoximinomethyldioxazine compounds and intermediates thereof, and to process for the preparation of the alkoximinomethyldioxazine compounds and intermediates thereof. The alkoximinomethyldioxazine compounds have the structure:

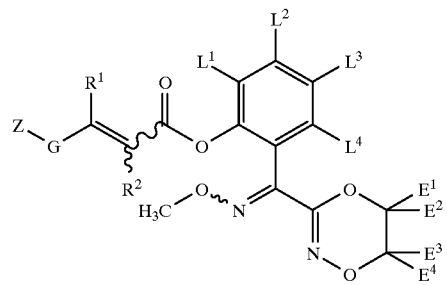

15 Claims, No Drawings

FUNGICIDAL ALKOXIMINOMETHYLDIOXAZINE DERIVATIVES

The invention relates to novel alkoximinomethyldioxazine derivatives, to a process for their preparation and to their use as fungicides, and also to novel intermediates and to a plurality of processes for their preparation.

It is already known that certain alkoximinomethyldioxazine derivatives of a constitution similar to those described below have fungicidal properties (compare, for example, WO-A 9504728). However, the fungicidal activity of these compounds, in particular at low application rates, leaves something to be desired. The novel alkoximinomethyldioxazine derivatives of the general formula (I) have now been found

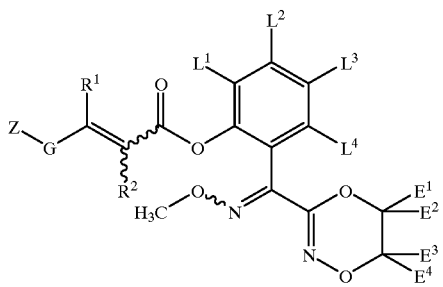

(I)

in which
G represents a single bond, alkanediyl which is optionally interrupted by heteroatoms (but where the carbon atom to which $R^1$ is attached is always linked to a carbon atom of the alkanediyl chain) or a grouping

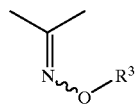

in which
$R^3$ represents in each case optionally substituted alkyl or cycloalkyl,
$R^1$ represents hydrogen, cyano or in each case optionally substituted alkyl or cycloalkyl,
$R^2$ represents hydrogen or in each case optionally substituted alkyl or cycloalkyl,
Z represents in each case optionally substituted alkyl, alkenyl, alkinyl, cycloalkyl, cycloalkenyl, aryl or heterocyclyl and
$E^1$, $E^2$, $E^3$ and $E^4$ are identical or different and, independently of one another, each represents hydrogen, alkyl, halogenoalkyl or hydroxyalkyl, or
$E^1$ and $E^2$ or $E^1$ and $E^3$ or $E^3$ and $E^4$ together with the respective carbon atoms to which they are attached form a cycloaliphatic ring and
$L^1$, $L^2$, $L^3$ and $L^4$, are identical or different and, independently of one another, each represents hydrogen, halogen, cyano, nitro, in each case optionally halogen-substituted alkyl, alkoxy, alkylthio, alkylsulphinyl or alkylsulphonyl.

In the definitions, the saturated or unsaturated hydrocarbon chains, such as alkyl, alkanediyl, alkenyl or Alkinyl, are in each case straight-chain or branched, including in combination with heteroatoms, such as in alkoxy, alkylthio or alkylamino. If an alkyl or alkanediyl chain is interrupted by more than one heteroatom, these can be identical or different. If an alkyl or alkanediyl chain is interrupted by more than one oxygen atom, two oxygen atoms are not directly adjacent.

Halogen generally represents fluorine, chlorine, bromine or iodine, and also pseudohalogens, such as, for example, cyano, preferably fluorine, chlorine, bromine or cyano, in particular fluorine or chlorine.

Aryl represents aromatic, mono or polycyclic hydrocarbon rings, such as, for example, phenyl, naphthyl, anthranyl, phenanthryl, preferably phenyl of naphthyl, in particular phenyl.

Heterocyclyl represents saturated or unsaturated, and also aromatic, cyclic compounds in which at least one ring member is a heteroatom, i.e. an atom different from carbon. If the ring contains a plurality of heteroatoms, these can be identical or different. Preferred heteroatoms are oxygen, nitrogen or sulphur. If appropriate, the cyclic compounds form a polycyclic ring system together with other carbocyclic or heterocyclic, fused-on or bridged rings. Preference is given to mono- or bicyclic ring systems, in particular to mono- or bicyclic aromatic ring systems.

Cycloalkyl represents saturated, carbocyclic, cyclic compounds which, if appropriate, form a polycyclic ring system with other carbocyclic, fused-on or bridged rings.

Furthermore, it has been found that the novel alkoximinomethyldioxazine derivatives of the general formula (I) are obtained when (process a) 3-(1-hydroxyphenyl-1-alkoximinomethyl)dioxazines of the general formula

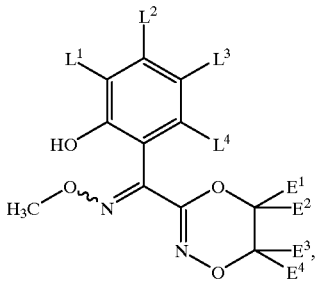

(II)

in which
$E^1$, $E^2$, $E^3$, $E^4$, $L^1$, $L^2$, $L^3$ and $L^4$ each as defined above, are reacted with an acrylic acid halide of the general formula (III)

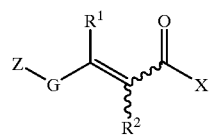

(III)

in which
G, $R^1$, $R^2$ and Z are each as defined above, and
X represents halogen,
if appropriate in the presence of a diluent and if appropriate in the presence of an acid acceptor.

Finally, it has been found that the novel alkoximinomethyldioxazine derivatives of the general formula (I) have very strong fungicidal activity.

The compounds according to the invention may, if appropriate, be present as mixtures of different possible isomeric forms, in particular of stereoisomers, such as, for example, 20

E- and Z- or optical isomers. What is claimed are both the E and the Z isomers, the individual enantiomers, the racemates, and also any mixtures of these isomers.

The present application preferably provides alkoximinomethyldioxazin derivatives of the formula (I) in which $R^1$ represents hydrogen, cyano or represents alkyl having 1 to 6 carbon atoms which is optionally substituted by halogen or alkoxy having 1 to 4 carbon atoms or represents cycloalkyl having 3 to 8 carbon atoms which is optionally substituted by halogen, alkyl or alkoxy having in each case 1 to 4 carbon atoms, $R^2$ represents hydrogen or represents alkyl having 1 to 6 carbon atoms which is optionally substituted by halogen or alkoxy having 1 to 4 carbon atoms or represents cycloalkyl having 3 to 8 carbon atoms which is optionally substituted by halogen, alkyl or alkoxy having in each case 1 to 4 carbon atoms, G represents a single bond, alkanediyl having 1 to 5 chain members which is optionally interrupted by one or two heteroatoms (but where the carbon atom to which $R^1$ is attached is always linked to a carbon atom of the alkanediyl chain) or a grouping

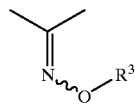

in which $R^3$ represents hydrogen or represents alkyl having 1 to 6 carbon atoms, alkenyl having 2 to 6 carbon atoms or alkinyl having 2 to 6 carbon atoms, each of which is optionally substituted by halogen or alkoxy having 1 to 4 carbon atoms, or represents cycloalkyl having 3 to 8 carbon atoms which is optionally substituted by halogen, alkyl or alkoxy having in each case 1 to 4 carbon atoms or represents arylalkyl having 1 to 4 carbon atoms in the alkyl moiety, which is optionally substituted in the aryl moiety, where the substituents are selected from the list below:

halogen, cyano, nitro, formyl, carbamoyl, thiocarbamoyl, in each case straight-chain or branched alkyl, alkoxy, alkylthio, alkylsulphinyl or alkylsulphonyl having in each case 1 to 6 carbon atoms, in each case straight-chain or branched alkenyl, alkenyloxy or alkinyloxy having in each case 2 to 6 carbon atoms, in each case straight-chain or branched halogenoalkyl, halogenoalkoxy, halogenoalkylthio, halogenoalkyl-sulphinyl or halogenoalkylsulphonyl having in each case 1 to 6 carbon atoms and 1 to 13 identical or different halogen atoms, in each case straight-chain or branched halogenoalkenyl or halogenoalkenyloxy having in each case 2 to 6 carbon atoms and 1 to 11 identical or different halogen atoms, in each case straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, in each case doubly attached alkylene or dioxyalkylene having in each case 1 to 6 carbon atoms and being in each case optionally mono- or polysubstituted by identical or different substituents selected from the group consisting of halogen and straight or branched halogenoalkyl having 1 to 4 carbon atoms and 1 to 9 identical or different halogen atoms, Z represents alkyl having 1 to 8 carbon atoms, which is optionally mono- or polysubstituted by identical or different substituents selected from the group consisting of halogen, cyano, hydroxyl, amino, $C_1$–$C_4$-alkoxy, $C_1$–$C_4$-alkylthio, $C_1$–$C_4$-alkylsulphinyl and $C_1$–$C_4$-alkylsulphonyl (each of which may optionally be substituted by halogen);

represents in each case optionally halogen-substituted alkenyl or alkinyl having in each case up to 8 carbon atoms; or represents phenyl, naphthyl, cycloalkyl or cycloalkenyl having in each case 3 to 8 carbon atoms and being in each case optionally mono- or polysubstituted by identical or different substituents, or represents heterocyclyl having 3 to 7 ring members, at least one of which represents oxygen, sulphur or nitrogen and another one or two of which optionally represent nitrogen, where the possible substituents are preferably selected from the list below:

halogen, cyano, nitro, amino, hydroxyl, formyl, carboxyl, carbamoyl, thiocarbamoyl;

in each case straight-chain or branched alkyl, alkoxy, alkylthio, alkylsulphinyl or alkylsulphonyl having in each case 1 to 6 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl or alkylsulphonyloxy, having in each case 1 to 6 carbon atoms in the individual alkyl moieties.

In each case doubly attached alkylene or dioxyalkylene having in each case 1 to 6 carbon atoms and being in each case optionally mono- or polysubstituted by identical or different substituents selected from the group consisting of halogen and, straight-chain or branched alkyl having 1 to 4 carbon atoms and straight-chain or branched halogenoalkyl having 1 to 4 carbon atoms and 1 to 9 identical or different halogen atoms;

Cycloalkyl having 3 to 8 carbon atoms;

heterocyclyl or heterocyclyl-methyl having in each case 3 to 7 ring members, 1 to 3 of which are in each case identical or different heteroatoms—in particular nitrogen, oxygen and/or sulphur—or a grouping

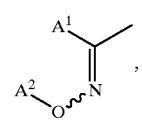

in which $A^1$ represents alkyl having 1 to 4 carbon atoms or cycloalkyl having 1 to 6 carbon atoms and A² represents optionally cyano-, alkoxy-, alkylthio-, alkylamino-, dialkylamino- or phenyl-substituted alkyl having 1 to 4 carbon atoms, alkenyl or alkinyl having in each case 2 to 4 carbon atoms and E¹, E², E³ and E⁴ are identical or different and, independently of one another each represents hydrogen, alkyl or hydroxyalkyl having in each case 1 to 4 carbon atoms or halogenoalkyl having 1 to 4 carbon atoms and 1 to five identical or different halogen atoms, or E¹ and E² or E¹ and E³ or E³ and E⁴ together with the respective carbon atoms to which they are attached form a cycloaliphatic ring having five, six or seven carbon atoms and L¹, L², L³ and L⁴ are identical or different and, independently of one another, each represents hydrogen, halogen, cyano, nitro, represents alkyl, alkoxy, alkylthio, alkylsulphinyl or alkylsulphonyl having in each case 1 to 6 carbon atoms and being in each case optionally substituted by 1 to 5 halogen atoms.

The present application relates in particular to compounds of the formula (I) in which R¹ represents hydrogen, cyano, methyl, ethyl, n- or i-propyl, n-, i-, s- or t-butyl, trifluoromethyl, trifluoroethyl, cyclopropyl, cyclobutyl, R² represents hydrogen, methyl, ethyl, n- or i-propyl, n-, i-, s- or t-butyl, trifluoromethyl, trifluoroethyl, cyclopropyl, cyclobutyl, G represents a single bond, methanediyl, 1,1-ethanediyl, 1,2-ethanediyl, 1,1-, 1,2-, 1,3- or 2,2-propanediyl, 1,1-, 1,2-, 1,3-, 1,4-, 2,2-, 2,3-butanediyl or 1,1-, 1,2- or 1,3-(2-methyl-propanediyl), —O—CH₂— (where Z is linked to the oxygen atom), Z
represents methyl, ethyl, n- or i-propyl, n-, i-, s- or t-butyl, each of which is optionally mono- to trisubstituted by identical or different substituents selected from the group consisting of chlorine fluorine, bromine, cyano, hydroxyl, amino, methoxy, ethoxy, methylthio, ethylthio, methylsulphinyl, ethylsulphinyl, methylsulphonyl, ethylsulphonyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl;

represents phenyl, cyclopropyl, cyclobutyl, cyclopentyl, cylohexyl, cycloheptyl, oxazolyl, benzofuranmyl, 1,2,4-thiadiazolyl, 1,3,4-thiadiazolyl, 1,2,4-oxadiazolyl, 1,3,4-oxadiazolyl, pyridinyl, pyrimidyl, pyridazinyl, pyrazinyl, 1,2,3-triazinyl, 1,2,4-triazinyl, 1,3,5-triazinyl or 5,6-dihydro-1,4,2-dioxazinyl, each of which is optionally mono- to trisubstituted by identical or different substituents, where the possible substituents are preferably selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, in each case doubly attached methylenedioxy, ethylenedioxy, each of which is optionally mono- to tetrasubstituted by identical or different substituents selected from the group consisting of fluorine, chlorine, methyl, trifluoromethyl and ethyl or a grouping

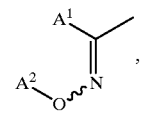

where
A¹ represents methyl, ethyl, n- or i-propyl, n-, i-, s- or t-butyl, cyclopropyl or cyclobutyl and
A² represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl and E¹, E², E³ and E⁴ are identical or different and, independently of one another, each represents hydrogen, methyl, ethyl, n- or i-propyl, n-, i-, s- or t-butyl, hydroxymethyl, trifluoromethyl or trifluoroethyl, or E¹ and E² or E¹ and E³ or E³ and E⁴ together with the respective carbon atoms to which they are attached form a cycloaliphatic ring having five, six or seven carbon atoms and L¹, L², L³ and L⁴ are identical or different and, independently of one another, each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

The present application likewise relates in particular to compounds of the formula (I) in which R¹ represents hydrogen, cyano, methyl, ethyl, n- or i-propyl, n-, i-, s- or t-butyl, trifluoromethyl, trifluoroethyl, cyclopropyl, cyclobutyl, R² represents hydrogen, methyl, ethyl, n- or i-propyl, n-, i-, s- or t-butyl, trifluoromethyl, trifluoroethyl, cyclopropyl, cyclobutyl, G represents a grouping

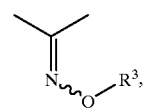

in which
R³
represents hydrogen or represents methyl, ethyl, n- or i-propyl, n-, -i-, s- or t-butyl, each of which is optionally mono- to trisubstituted by fluorine, chlorine, bromine, methoxy, ethoxy, (each of which is optionally substituted by fluorine and/or chlorine), represents allyl, crotonyl, 1-methyl-allyl, propargyl or 1-methyl-propargyl, each of which is optionally mono- to trisubstituted by fluorine or chlorine;

represents cyclopropyl, cyclobutyl, cyclopentyl or cyclohexyl, each of which is optionally mono- to hexasubstituted by fluorine, chlorine, bromine, methoxy, ethoxy, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy), methyl, ethyl, n- or i-propyl;

represents benzyl, phenyl-1-ethyl or phenyl-2-ethyl, each of which is optionally mono- to trisubstituted in the phenyl moiety, where the possible substituents are preferably selected from the list below:
Fluorine, chlorine, bromine, cyano, nitro, methyl, ethyl, n- or i-propyl, n-, i- s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl;
in each case doubly attached trimethylene (propane-1,3-diyl), methylenedioxy or ethylenedioxy, each of which is optionally mono- or polysubstituted by identical or different substituents selected from the group consisting of fluorine, chlorine, methyl, trifluoromethyl, ethyl, n- or i-propyl, Z
represents methyl, ethyl, n- or i-propyl, n-, i-, s- or t-butyl, each of which is optionally mono- to trisubstituted by identical or different substituents selected from the group consisting of chlorine fluorine, bromine, cyano, hydroxyl, amino, methoxy, ethoxy, methylthio, ethylthio, methylsulphinyl, ethylsulphinyl, methylsulphonyl, ethylsulphonyl, difluoromethoxy, trifluoromethoxy, difluorochloromethoxy, trifluoroethoxy, difluoromethylthio, trifluoromethylthio, difluorchloromethylthio, trifluoromethylsulphinyl or trifluoromethylsulphonyl;

represents vinyl, allyl or propargyl, each of which is optionally mono- to trisubstituted by identical or different substituents selected from the group consisting of chlorine fluorine or bromine; or represents phenyl, cyclopropyl, cyclobutyl, cyclopentyl, cyclohexyl, cycloheptyl, 1,2-oxazolyl, benzofuranyl, 1,2,4-thiadiazolyl, 1,3,4-thiadiazolyl, 1,2,4-oxadiazolyl, 1,3,4-oxadiazolyl, pyridinyl, pyrimidyl, pyridazinyl, pyrazinyl, 1,2,3-triazinyl, 1,2,4-triazinyl, 1,3,5-triazinyl or 5,6-dihydro-1,4,2-dioxazinyl, each of which is optionally mono- to trisubstituted by identical or different substituents, where the possible substituents are preferably selected from the list below:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl,
in each case doubly attached methylenedioxy, ethylenedioxy, each of which is optionally mono- to tetrasubstituted by identical or different substituents selected from the group consisting of fluorine, chlorine, methyl, trifluoromethyl or ethyl or a grouping

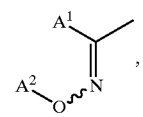

where
$A^1$ represents methyl, ethyl, n- or i-propyl, n-, i-, s- or t-butyl, cyclopropyl or cyclobutyl and
$A^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl and $E^1$, $E^2$, $E^3$ and $E^4$ are identical or different and, independently of one another, each represents hydrogen, methyl, ethyl, n- or i-propyl, n-, i-, s- or t-butyl, hydroxymethyl, trifluoromethyl or trifluoroethyl, or $E^1$ and $E^2$ or $E^1$ and $E^3$ or $E^3$ and $E^4$ together with the respective carbon atoms to which they are attached form a cycloaliphatic ring having five, six or seven carbon atoms and $L^1$, $L^2$, $L^3$ and $L^4$ are identical or different and, independently of one another, each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

A particularly preferred group of compounds according to the invention are the compounds of the formula (I) in which $R^1$ represents cyclopropyl or, in particular, methyl,
$R^2$ represents hydrogen,
G represents a single bond or —O—CH$_2$— (where Z is attached to the oxygen atom),
Z
represents methyl, ethyl, n- or i-propyl, n-, i-, s- or t-butyl, each of which is optionally mono- to trisubstituted by identical or different constituents selected from the group consisting of chlorine fluorine, bromine, cyano, hydroxyl, amino, methoxy, ethoxy, methylthio, ethylthio, methylsulphinyl, ethylsulphinyl, methylsulphonyl, ethylsulphonyl, difluoromethoxy, trifluoromethoxy, difluorochloromethoxy, trifluoroethoxy, difluoromethylthio, trifluoromethylthio, difluorochloromethylthio, trifluoromethylsulphinyl and trifluoromethylsulphonyl; or represents 1,2-oxazolyl, benzofuranyl or phenyl which is optionally mono- to trisubstituted by identical or different substituents, where the possible substituents are preferably selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, or represents in each case doubly attached methylenedioxy, ethylenedioxy, each of which is optionally mono- to tetrasubstituted by identical or different substituents selected from the group consisting of fluorine, chlorine, methyl, trifluoromethyl and ethyl or a grouping

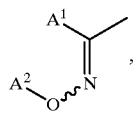

where
A$^1$ represents methyl, ethyl, n- or i-propyl, n-, i-, s- or t-butyl, cyclopropyl or cyclobutyl and
A$^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl, E$^1$ and E$^2$ are identical or different and, independently of one another, each represents methyl, or in particular, hydrogen, E$^3$ and E$^4$ each represents hydrogen, L$^1$ and L$^3$ are identical or different and, independently of one another, each represents methyl, or in particular, hydrogen and L$^2$ and L$^4$ each represents hydrogen.

Another particularly preferred group of compounds according to the invention are those compounds of the formula (I) in which R$^1$ represents cyclopropyl or, in particular, methyl, R$^2$ represents hydrogen, G represents a grouping

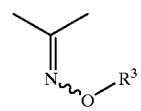

in which
R$^3$ represents methyl or represents benzyl which is optionally mono- to trisubstituted in the phenyl moiety by fluorine, chlorine, bromine, cyano, nitro, methyl or methoxy, Z
represents methyl, ethyl, n- or i-propyl, n-, i-, s- or t-butyl, trifluoromethyl, trifluorethyl, methoxymethyl, methylthiomethyl or methylsulphonylmethyl, vinyl, dichlorovinyl, allyl, propargyl, cyclopropyl, methylcyclopropyl, cyclobutyl, cyclopentyl, cylohexyl or represents 1,2-oxazolyl, benzofuranyl or, in particular, phenyl each of which is optionally mono- to trisubstituted by identical or different substituents, where the possible substituents are preferably selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorchloromethoxy, trifluorethoxy, difluoromethylthio, trifluoromethylthio, difluorochloromethylthio, trifluoromethylsulphinyl or trifluoromethylsulphonyl, methoxycarbonyl, ethoxycarbonyl; or represents in each case doubly attached methylenedioxy, ethylenedioxy, each of which is optionally mono- to tetrasubstituted by identical or different substituents selected from the group consisting of fluorine, chlorine, methyl, trifluoromethyl and ethyl or a grouping

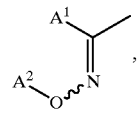

where
A$^1$ represents methyl, ethyl, n- or i-propyl, n-, i-, s- or t-butyl, cyclopropyl or cyclobutyl and
A$^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl, E$^1$ and E$^2$ are identical or different and, independently of one another, each represents methyl, or in particular, hydrogen, E$^3$ and E$^4$ each represents hydrogen, L$^1$ and L$^3$ are identical or different and, independently of one another, each represents methyl, or in particular, hydrogen and L² and L⁴ each represents hydrogen.

The abovementioned general or preferred radical definitions apply both to the end products of the formula (I) and, correspondingly, to the starting materials or intermediates required in each case for the preparation.

Independently of the combination given in each case, the definitions of radicals given in the combinations or preferred combinations of radicals in question specifically for these radicals are also replaced at will by definitions of radicals of the other preferred ranges in question.

The formula (II) provides a general definition of the 3-(1-hydroxyphenyl-1-alkoxirninomethyl)dioxazines required as starting materials for carrying out the process a) according to the invention. In this formula (II), $E^1$, $E^2$, $E^3$, $E^4$, $L^1$, $L^2$, $L^3$ and $L^4$ each preferably or in particular have those meanings which have already been mentioned in connection with the description of the compounds of the formula (I) according to the invention as being preferred or as being particularly preferred for $E^1$, $E^2$, $E^3$, $E^4$, $L^1$, $L^2$, $L^3$ and $L^4$.

The 3-(1-hydroxyphenyl-1-alkoximinomethyl)dioxazines of the formula (II) are known and can be prepared by known processes (WO 95-04728).

The formula (III) provides a general definition of the acrylic acid halides furthermore required as starting materials for carrying out the process a) according to the invention. In this formula (III) G, $R^1$, $R^2$ and Z each preferably or in particular have those meanings which have already been mentioned in connection with the description of the compounds of the formula (I) according to the invention as being preferred or as being particularly preferred for G, $R^1$, $R^2$ and Z. X represents halogen, preferably chlorine.

Some of the acrylic acid halides of the formula (III) are known (Balsamo, A.; Crotti, P.; Lapucci, A.; Macchia, B.; Macchia, F.; et al., J.Med.Chem., 24, 5, 1981, 525–532) and/or they can be prepared by processes known per se from the corresponding acrylic acids (compare, for example, Padmanathan,T.; Sultanbawa, M. U. S., J.Chem.Soc., 1963, 4210–4218 or Wiley; van der Plas, J.Chem.Eng.Data, 10, 1965, 72) by halogenation with customary halogenating agents, such as, for example, thionyl chloride or oxalyl chloride.

Novel, and also part of the subject matter of the present application, are acrylic acid halides of the general formula (III-a)

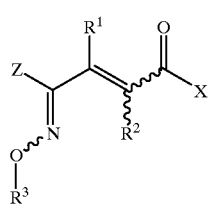

(III-a)

in which $R^1$, $R^2$, $R^3$, X and Z are each as defined above.

The acrylic acid halides of the formula (III-a) are obtained when (process b) acrylic acids of the general formula (IV)

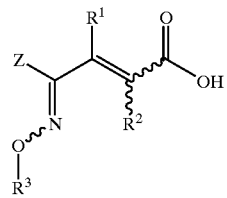

(IV)

in which $R^1$, $R^2$, $R^3$ and Z are each as defined above are reacted with an halogenating agent, such as, for example, thionyl chloride, phosgene, phosphorus pentachloride or phosphorus oxychloride, if appropriate in the presence of a diluent, such as, for example, 1,2-dichloroethane, at temperatures of from 0 to 150° C. (compare also the preparation examples).

The formula (IV) provides a general definition of the acrylic acids required as starting materials for carrying out the process b) according to the invention. In this formula (IV), $R^1$, $R^2$, $R^3$ and Z each preferably or in particular have those meanings which have already been mentioned in connection with the description of the compounds of the formula (I) according to the invention as being preferred or as being particularly preferred for $R^1$, $R^2$, $R^3$ and Z.

As novel substances, the acrylic acids of the formula (IV) also form part of the subject matter of the present application. They are obtained when (process c) acrylic esters of the formula (V)

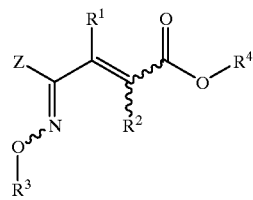

(V)

in which $R^1$, $R^2$, $R^3$ and Z are each as defined above and $R^4$ represents alkyl are hydrolyzed, if appropriate in the presence of a diluent, for example an alcohol, such as methanol or ethanol, if appropriate in the mixture with water, and if appropriate in the presence of a base, such as, for example, sodium hydroxide or potassium hydroxide, or an acid, such as, for example, hydrochloric acid or sulphuric acid.

The formula (V) provides a general definition of the acrylic esters required as starting materials for carrying out the process c) according to the invention. In this formula (V), $R^1$, $R^2$, $R^3$ and Z each preferably or in particular have those meanings which have already been mentioned in connection with the description of the compounds of the formula (I) according to the invention as being preferred or as being particularly preferred for $R^1$, $R^2$, $R^3$ and Z. $R^4$ represents alkyl, preferably methyl or ethyl.

As novel substances, the acrylic esters of the formula (V) also form part of the subject matter of the present application. They are obtained when (process d) α-diketone monooximes of the formula (VI)

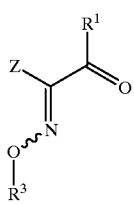

(VI)

in which
R¹, R³ and Z are each as defined above
are reacted with a dialkyl alkoxycarbonylmethanephosphonate of the formula (VII)

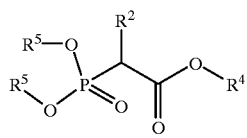

in which
R² and R⁴ are each as defined above and
R⁵ represents alkyl,
if appropriate in the presence of a diluent, for example an ether, such as tetrahydrofuran, and if appropriate in the presence of a base, such as, for example, potassium t-butoxide or sodium hydride.

The formula (VI) provides a general definition of the α-diketone monooximes required as starting materials for carrying out the process d) according to the invention. In this formula (VI), R¹, R³ and Z each preferably or in particular have those meanings which have already been mentioned in connection with the description of the compounds of the formula (I) according to the invention as being preferred or as being particularly preferred for R¹, R³ and Z.

The α-diketone monooximes of the formula (VI) are known and/or can be prepared by known methods (compare, for example, Diels; Stern, Chem.Ber., 40 (1907),1624).

The formula (VII) provides a general definition of the dialkyl alkoxycarbonylmethanephosphonate furthermore required as starting materials for carrying out the process d) according to the invention. In this formula (VII), R² and R⁴ each preferably or in particular have those meanings which have already been mentioned in connection with the description of the compounds of the formula (I) according to the invention as being preferred or particularly preferred for R² and R⁴. R⁵ represents alkyl, preferably methyl or ethyl. The dialkyl alkoxycarbonylmethanephosphonates of the formula (VII) are known chemicals for synthesis.

Suitable diluents for carrying out the process a) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2- dimethoxyethane, 1,2-diethoxyethane or anisol; amides, such as N,N-dimethylformamide, N,N-dimethylacetamide, N-methylformanilide, N-methylpyrrolidone or hexamethylphosphoric triamide; Esters such as methyl acetate or ethyl acetate; sulphones, such as sulpholane, and also amines, such as pyridine.

The process a) according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process a) according to the invention, the reaction temperatures can be varied within a relatively wide range. In general, the reaction is carried out at temperatures from 0° C. to 150° C., preferably at temperatures from 0° C. to 80° C.

When carrying out the process a) according to the invention for preparing the compounds of the formula (I), generally from 1 to 15 mol, preferably from 1 to 8 mol, of an acrylic acid halide of the formula (III) are employed per mole of 3-(1-hydroxyphenyl-1-alkoximinomethyl) dioxazine of the formula (II).

The processes according to the invention are generally carried out under atmospheric pressure. However, it is also possible to operate under elevated or reduced pressure—in general between 0.1 bar and 10 bar.

The compounds according to the invention have a potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not in a limiting way:

Xanthomonas species, such as, for example, *Xanthomonas campestris* pv. *oryzae;*
Pseudomonas species, such as, for example, *Pseudomonas syringae* pv. *lachrymans;*
Erwinia species, such as, for example, *Erwinia amylovora;*
Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*
Bremia species, such as, for example, *Bremia lactucae,*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*

Venturia species, such as, for example, *Venturia inaequalis;*
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus;*
Puccinia species, such as, for example, *Puccinia recondita;*
Sclerotinia species, such as, for example, *Sclerotinia sclerotiorum*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;*
Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling cereal diseases, such as, for example, against Leptosphaeria species, for controlling diseases in viticulture and fruit and vegetable growing, such as, for example, against Venturia and Plasmopara species. or for controlling rice diseases, such as, for example, against Pyricularia species. Other cereal diseases, such as, for example, Septoria, Pyrenophora or Cochliobolus species, are controlled very successfully.

Furthermore, the compounds according to the invention may also be employed to increase the yield of crops. Moreover, they exhibit reduced toxicity and are tolerated well by plants.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, the following are suitable for use as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied, gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

Depending on their particular physical and/or chemical properties, the active compounds can be converted into the customary formulations such as solutions, emulsions, suspensions, powders, foams, pastes, granules, aerosols and microencapsulations in polymeric substances and in coating compositions for seeds, and ULV cool and warm fogging formulations.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:
Fungicides
aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-b-propyl-1H-1,2,4-triazole-1-ethanol,

α-(2,4-dichlorophenyl)-β-methoxy-a-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)ethanone-O-(phenylmethyl)-oxime, 1-(2-methyl-1-naphthalenyl)-1H-pyrrol-2,5-dione, 1-(3,5-dichlorophenyl)-3-(2-propenyl)-2,5-pyrrolidindione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)sulphonyl]-5-(trichloromethyl)-1,3,4-thiadiazole, 2-[[6-deoxy-4-O-(4-O-methyl-β-D-glycopyranosyl)-a-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrol-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulfonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethylmorpholinehydrochloride, ethyl [(4-chlorophenyl)-azo]-cyanoacetate, potassium hydrogen carbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulfonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
Bactericides bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/Acaricides/Nematicides abamectin, acephate, acrinathrin, alanycarb, aldicarb, alphamethrin, amitraz, avermectin, AZ 60541, azadirachtin, azinphos A, azinphos M, azocyclotin,

*Bacillus thuringiensis*, 4-bromo-2-(4-chlorophenyl)-1-(ethoxymethyl)-5-(tri-fluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen,
quinalphos, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

It is also possible to admix other known active compounds, such as herbicides, fertilizers and growth-promoting substances.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, dusting, foaming, brushing on and the like. It is further possible to apply the active compounds by the ultra-low volume method or to inject the active compound formulation, or the active compound itself, into the soil. The seed of the plants can also be treated.

When the active compounds according to the invention are employed as fungicides, the application rates can be varied within a relatively wide range, depending on the type of application. For the treatment of parts of plants, the active compound application rates are generally between 0.1 and 10,000 g/ha, preferably between 10 and 1000 g/ha. For the treatment of seeds, the active compound application rates are generally between 0.001 and 50 g per kilogram of seeds, preferably between 0.01 and 10 g per kilogram of seeds. For the treatment of the soil, the active compound application rates are generally between 0.1 and 10,000 g/ha, preferably between 1 and 5000 g/ha.

PREPARATION EXAMPLES

EXAMPLE 1

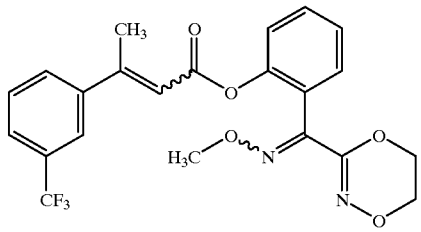

Process a)

0.69 g (0.003 mol) of 3-(3-trifluoromethyl-phenyl)-but-2-enoic acid, 0.39 g (0.0033 mol) of thionyl chloride and 10 ml of 1,2-dichloroethane are boiled under reflux for one hour. Volatile components are distilled off under reduced pressure and the residue, the crude 3-(3-trifluoromethyl-phenyl)-but-2-enoyl chloride, is dissolved in 20 ml of dimethylformamide. This solution is added dropwise to a mixture of 0.62 g (0.0027 mol) of (5,6-dihydro-[1,4,2]dioxazin-3-yl)-(2-hydroxy-phenyl)-methanone O-methyl-oxime and 0.848 g (0.0028 mol) of an 80% strength sodium hydride suspension in 30 ml of dimethylformamide, and stirring is continued for another 16 hours. The reaction mixture is then poured into 50 ml of water and extracted twice with 50 ml of ethyl acetate each time, the organic phase is dried over sodium sulphate and the solvent is distilled off under reduced pressure. The residue is chromatographed over silica gel using ethyl acetate/cyclohexane (1:1). This gives 0.99 g (82% of theory) of 2-[(5,6-dihydro-[1,4,2]dioxazin-3-yl)-methoxyiminomethyl]-phenyl 3-(3-trifluoromethylphenyl)-but-2-enoate.

¹H-NMR-Spectrum (CDCl₃/TMS): δ=2.64 (s, 3H); 3.94 (s, 3H); 4.17 (m, 2H); 4.48 (m, 2H); 6.34 (s, 1H); 7.26–7.78 (m, 8H) ppm.

Preparation of the Starting Material

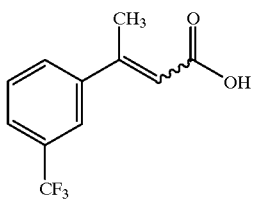

34 g (0.139 mol) of methyl 3-(3-trifluoromethyl-phenyl)-but-2-enoate are dissolved in 200 ml of methanol, admixed with 24.8 g (0.28 mol) of 45% strength aqueous sodium hydroxide solution and stirred at 20° C. for 16 hours. The solvent is distilled off under reduced pressure and the residue is taken up in 100 ml of water, acidified using approximately 150 ml of 2N hydrochloric acid (pH≈1) and extracted twice with 50 ml of ethyl acetate each time. The organic phase is dried over sodium sulphate, the solvent is distilled off under reduced pressure and the residue is stirred with petroleum ether. This gives 17 g (53% of theory) of 3-(3-trifluoromethyl-phenyl)-but-2-enoic acid.

¹H-NMR spectrum (CDCl₃/TMS): δ=2.62 (d, 3H); 6.19 (q, 1H); 7.48–7.55 (1H); 7.64–7.73 (3H) ppm.

Preparation of the Precursor

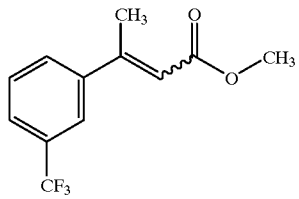

At 0° C., 33.2 g (0.183 mol) of dimethyl methoxycarbonylmethanephosphonate are added dropwise to a solution of 20.5 g (0.183 mol) of potassium tert-butoxide in 200 ml of tetrahydrofuran. At 20° C., 31.2 g (0.166 mol) of 3-(trifluoromethyl)-acetophenone are added dropwise, and the mixture is subsequently boiled under reflux for three hours. The solvent is distilled off under reduced pressure, and the residues are mixed with 200 ml of water and extracted twice with 100 ml of ethyl acetate each time. The organic phase is dried over sodium sulphate and the solvent is distilled off under reduced pressure. The product is then distilled at 0.5 torr and 80–90° C. This gives 34.6 g (85.4% of theory) of methyl 3-(3-trifluoromethyl-phenyl)-but-2-enoate as a mixture of stereoisomers.

¹H-NMR-spectrum (CDCl₃/TMS): δ=2.20 (d, 3H, Z isomer); 2.59 (d, 3H, E isomer); 3.56 (3H, Z isomer); 3.77 (3H, E isomer); 5.98 (q, 1H, Z isomer); 6.16 (q, 1H, E isomer); 7.27–8.22 (4H) ppm.

EXAMPLE 2

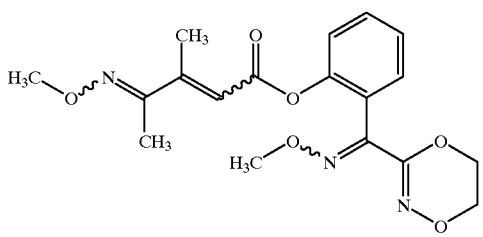

Process a)

180 mg (0.0045 mol) of a 60% strength sodium hydride suspension are added to a solution of 1.08 g (0.0046 mol) of (5,6-dihydro-[1,4,2]dioxazin-3-yl)-(2-hydroxy-phenyl)-methanone O-methyl-oxime in 5 ml of dimethylformamide, and the mixture is stirred until evolution of gas ceases. At 0° C., 0.8 g (0.0045 mol) of 4-methoxyimino-3-methyl-pent-2-enoic chloride is added dropwise. The reaction mixture is allowed to stand for 10 minutes and poured into water, and the mixture is extracted with 10 ml of ethyl acetate. The organic phase is dried over sodium sulphate and the volatile components are distilled off under reduced pressure. The residue is stirred with petroleum ether. This gives 2.09 g (32.6% of theory) of 2-[(5,6-dihydro-[1,4,2]dioxazin-3-yl)-methoxyiminomethyl]-phenyl ester 4-methoxyimino-3-methylpent-2-enoate as oil.

¹H-NMR spectrum (CDCl₃/TMS): δ=2.03 (3H); 2.41 (d, 3H); 3.92 (3H); 4.00 (3H); 4.09–4.17 (2H); 4.45–4.48 (2H); 6.24 (q, 1H), 7.25–7.32 (3H); ppm.

Preparation of the Starting Material

EXAMPLE (III-a-1)

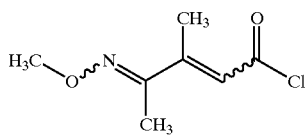

Process b)

1.6 g (0.01 mol) of 4-methoxyimino-3-methylpent-2-enoic acid and 1.8 g (0.015 mol) of thionyl chloride in 10 ml of dichloroethane are heated under reflux for 30 minutes. Volatile components are distilled off under reduced pressure and the residue is distilled under high vacuum. This gives 0.8 g (45% of theory) of 4-methoxyimino-3-methylpent-2-enoic chloride as a mixture of stereoisomers.

¹H-NMR spectrum (CDCl₃/TMS): δ=2.00 (3H, isomer A+isomer B); 2.11/2.12 (d, 3H, isomer B); 2.33/2.33 (d, 3H, isomer A); 3,92 (3H, isomer B); 4.02 (3H, isomer A); 5.88 (1H, isomer B); 6.36/6.37 (q, 1H, isomer A) ppm.

Preparation of the Precursor

EXAMPLE (IV-1)

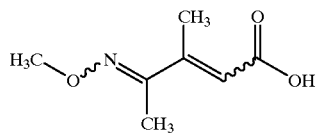

Process c)

35.8 g (0.209 mol) of methyl 4-methoxyimino-3-methylpent-2-enoate are dissolved in 600 ml of methanol, admixed with 300 ml of 2N sodium hydroxide solution and boiled under reflux for 30 minutes. The solvent is distilled off under reduced pressure and the residue is taken up in 300 ml of water and acidified with approximately 350 ml of 2N hydrochloric acid (pH≈1). The product precipitates out and is filtered off. This gives 18.2 g (55.4% of theory) of 4-methoxyimino-3-methylpent-2-enoic acid as the mixture of the stereoisomers.

$^1$H-NMR spectrum (CDCl$_3$/TMS): δ=2.00 (s, 3H, isomer A); 2.01 (s, 3H, isomer B); 2.06/2.07 (d, 3H, isomer B); 2,37 (d, 3H, isomer A); 3.90 (s, 3H, isomer B); 3.99 (s, 3H, isomer A); 5.59 (1H, isomer B); 6.10 (q, 1H, isomer A) ppm.

Preparation of the Precursor

EXAMPLE (V-1)

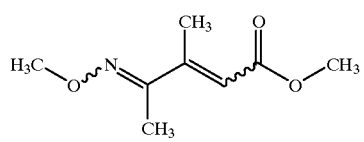

Process d)

At 0° C., 12.4 g (0.068 mol) of dimethyl methoxycarbonylmethanephosphonate are added dropwise to a solution of 7.63 g (0.068 mol) of potassium tert-butoxide in 70 ml of tetrahydrofuran. At 20° C., 7.83 g (0.068 mol) of butane-2,3-dione mono-(O-methyl-oxime) are then added dropwise, and the mixture is subsequently boiled under reflux for 30 minutes. The solvent is distilled off under reduced pressure and the residue is mixed with 50 ml of water and extracted twice with 50 ml of diethyl ether each time. The organic phase is dried over sodium sulphate and the solvent is distilled off under reduced pressure. The product is then distilled at 17 torr. This gives 5.16 g (44% of theory) of methyl 4-methoxyimino-3-methylpent-2-enoate as a mixture of stereoisomers with a boiling range of from 95 to 105° C.

$^1$H-NMR spectrum (CDCl$_3$/TMS): δ=1.98 (s, 3H, isomer A); 2.00 (s, 3H, isomer B); 2.03 (d, 3H, isomer B); 2.35 (d, 3H, isomer A); 3.69 (s, 3H, isomer B); 3.74 (s, 3H, isomer A); 3.89 (s, 3H, isomer B); 3.98 (s, 3H, isomer A); 5.83 (q, 1H, isomer B); 6.08 (q, 1H, isomer A) ppm.

The compounds of the formula (I-a) according to the invention listed in Table 1 below are also obtained by the methods of Examples (1) and (2), and in accordance with the general description of the preparation process a) according to the invention:

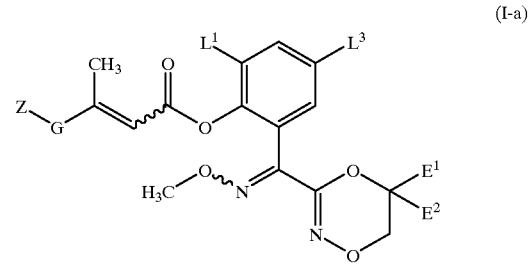

(I-a)

TABLE 1

| Ex. No. | Z | G | $E^1$ | $E^2$ | $L^1$ | $L^3$ | phys. data |
|---|---|---|---|---|---|---|---|
| 3 | 3-trifluoromethylphenyl | —O—CH$_2$— | —H | —H | —H | —H | |
| 4 | 3-bromophenyl | — | —H | —H | —H | —H | logP: 3.72 |
| 5 | 3-methoxyphenyl | — | —H | —H | —H | —H | logP: 3.22 |
| 6 | phenyl | — | —H | —H | —H | —H | logP: 3.22 |
| 7 | 4-trifluoromethyl | — | —H | —H | —H | —H | logP: 3.81 |
| 8 | 4-tolyl | — | —H | —H | —H | —H | logP: 3.58 |
| 9 | 3-ethylphenyl | — | —H | —H | —H | —H | logP: 3.91 |
| 10 | 4-bromophenyl | — | —H | —H | —H | —H | logP: 3.78 |
| 12 | 4-ethoxyphenyl | — | —H | —H | —H | —H | logP: 3.57 |
| 13 | 4-tolyl | — | —H | —H | —H | —H | logP: 4.06 |
| 14 | 2,5-dichlorophenyl | — | —H | —H | —H | —H | logP: 3.93 |
| 15 | 4-chlorophenyl | — | —H | —H | —H | —H | |
| 16 | 3,4-dichlorophenyl | — | —H | —H | —H | —H | |
| 17 | 3-tolyl | — | —H | —H | —H | —H | logP: 3.58 |
| 18 | 3,4-dimethoxyphenyl | — | —H | —H | —H | —H | |
| 19 | 3-chlorophenyl | — | —H | —H | —H | —H | logP: 3.64 |
| 20 | 4-fluorophenyl | — | —H | —H | —H | —H | logP: 3.28 |
| 21 | 4-methoxyphenyl | — | —H | —H | —H | —H | logP: 3.19 |
| 22 | 4-trifluoromethyl | — | —CH$_3$ | —H | —H | —H | logP: 4.02 |
| 23 | 4-trifluoromethyl | — | —CH$_3$ | —CH$_3$ | —H | —H | logP: 4.23 |
| 24 | 2-(i-propoxy)phenyl | — | —H | —H | —H | —H | logP: 3.87 |
| 25 | 2-ethoxyphenyl | — | —H | —H | —H | —H | logP: 3.63 |
| 26 | 2-propoxyphenyl | — | —H | —H | —H | —H | logP: 3.98 |
| 27 | (2-benzofuranyl) | — | —H | —H | —H | —H | |
| 28 | 2-chlorophenyl | — | —H | —H | —H | —H | |
| 29 | 2-fluorophenyl | — | —H | —H | —H | —H | logP: 3.25 |
| 30 | 4-methoxyphenyl | —O—CH$_2$— | —H | —H | —H | —H | |
| 31 | 4-tolyl | —O—CH$_2$— | —H | —H | —H | —H | |
| 32 | 3-chlorophenyl | — | —H | —H | —H | —CH$_3$ | logP: 3.90 |

TABLE 1-continued

| Ex. No. | Z | G | E¹ | E² | L¹ | L³ | phys. data |
|---|---|---|---|---|---|---|---|
| 33 | phenyl | H₃C-O-N=C(CH₃)- | —H | —H | —H | —H | |
| 34 | 4-fluorophenyl | H₃C-O-N=C(CH₃)- | —H | —H | —H | —H | |
| 35 | 4-chlorophenyl | H₃C-O-N=C(CH₃)- | —H | —H | —H | —H | |
| 36 | 3-chlorophenyl | H₃C-O-N=C(CH₃)- | —H | —H | —H | —H | |
| 37 | 4-tolyl | H₃C-O-N=C(CH₃)- | —H | —H | —H | —H | |
| 38 | 4-cyanophenyl | H₃C-O-N=C(CH₃)- | —H | —H | —H | —H | |
| 39 | 3-cyanophenyl | H₃C-O-N=C(CH₃)- | —H | —H | —H | —H | |
| 40 | 3,5-dimethylisoxazol-3-yl | H₃C-O-N=C(CH₃)- | —H | —H | —H | —H | |
| 41 | i-propyl | H₃C-O-N=C(CH₃)- | —H | —H | —H | —H | |
| 42 | 2-methoxyphenyl | — | —H | —H | —H | —H | logP: 3.28 |
| 43 | 2-trifluorophenyl | — | —H | —H | —H | —H | logP: 3.58 |
| 44 | 2,5-dimethylphenyl | — | —H | —H | —H | —H | logP: 3.85 |
| 45 | 2-bromophenyl | — | —H | —H | —H | —H | logP: 3.58 |
| 46 | 6-chloro-3-methylpyridin-2-yl | — | —H | —H | —H | —H | logP: 2.75 |
| 47 | 2-methylphenyl | — | —H | —H | —H | —H | logp: 3.48 |

Use Examples

EXAMPLE A

Plasmopara Test (Grapevine)/Protective
Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, the young plants are sprayed with the preparation of active compound at the stated application rate. After the spray coating has dried on, the plants are inoculated with an aqueous spore suspension of *Plasmopara viticola* and then remain in an incubation cabin at approximately 20° C. and 100% relative atmospheric humidity for 1 day. The plants are subsequently placed in a greenhouse at approximately 21° C. and approximately 90% relative atmospheric humidity for 5 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

In this test, for example, the following compounds of Preparation Examples (1), (4), (5), (6), (8) and (9) exhibit, at an exemplary active compound application rate of 100 g/ha, an efficacy of up to 100% in comparison with the untreated control.

EXAMPLE B

Venturia Test (Apple)/Protective
Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the causative organism of apple scab *Venturia inaequalis* and then remain in an incubation cabin at approximately 20° C. 100% relative atmospheric humidity for 1 day.

The plants are then placed in the greenhouse at approximately 21° C. and a relative atmospheric humidity of approximately 90%.

Evaluation is carried out 12 days after the inoculation. 0% means an efficacy which corresponds to that of the control, whereas an efficacy of 100% means that no infection is observed.

In this test, for example, the following compounds of Preparation Examples (1), (4), (5), (6), (7), (8) and (9) exhibit, at an exemplary active compound application rate of 10 g/ha, an efficacy of up to 100% in comparison with the untreated controls.

EXAMPLE C

Leptosphaeria Nodorum Test (Wheat)/Protective
Solvent: 10 parts by weight of N-methyl-pyrrolidone
Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a spore suspension of *Leptosphaeria nodorum*. The plants remain in an incubation cabin at 20° C. and 100% relative atmospheric humidity for 48 hours.

The plants are placed in a greenhouse at a temperature of approximately 15° C. and a relative atmospheric humidity of 80%.

Evaluation is carried out 10 days after the inoculation. 0% means an efficacy which corresponds to that of the control, whereas an efficacy of 100% means that no infection is observed.

In this test, for example, the following compound of the Preparation Examples (4) exhibits, at an exemplary active compound application rate of 25 g/ha, an efficacy of 70% in comparison with the untreated control.

EXAMPLE D

Pyricularia Test (Rice)/Protective
Solvent: 2.5 parts by weight of acetone
Emulsifier: 0.06 parts by weight of alkylaryl polyglycol ether To produce a suitable preparation of active compound, 1 part by weight of active compound is mixed with the stated amount of solvent and the concentrate is diluted with water and the stated amount of emulsifier to the diluted concentration.

To test for protective activity, young rice plants are sprayed with the preparation of active compound at the stated application rate. After the spray coating has dried on, the plants are inoculated with an aqueous spore suspension of *Pyricularia oryzae*. The plants are then placed in a greenhouse at 100% relative atmospheric humidity and 25° C.

Evaluation is carried out 4 days after the inoculation. 0% means an efficacy which corresponds to that of the control, whereas an efficacy of 100% means that no infection is observed.

In this test, for example, the following compounds of the Preparation Examples (3), (7), (8) and (9) exhibit, at an exemplary active compound application rate of 750 g/ha and a contact time of one day, an efficacy of more than 80% in comparison with the untreated control.

EXAMPLE E

Puccinia Test (Wheat)/Protective
Solvent: 25 parts by weight of N,N-dimethylacetamide
Emulsifier: 0.06 parts by weight of alkylaryl polyglycol ether To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Puccinia recondita*. The plants remain in an incubation cabin at 20° C. and 100% relative atmospheric humidity for 48 hours.

The plants are then placed in a greenhouse at temperature of approximately 20° C. and a relative atmospheric humidity of 80% to promote the development of crude pustules.

Evaluation is carried out 10 days after the inoculation. 0% means an efficacy which corresponds to that of the control, whereas an efficacy of 100% means that no infection is observed.

What is claimed is:
1. Compounds of the formula (I)

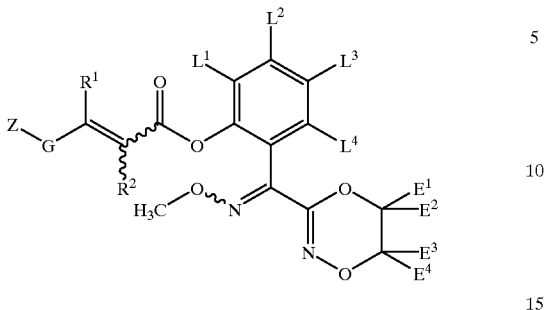

in which
- R¹ represents hydrogen, cyano or represents alkyl having 1 to 6 carbon atoms which is optionally substituted by halogen or alkoxy having 1 to 4 carbon atoms or represents cycloalkyl having 3 to 8 carbon atoms which is optionally substituted by halogen, alkyl or alkoxy having in each case 1 to 4 carbon atoms,
- R² represents hydrogen or represents alkyl having 1 to 6 carbon atoms which is optionally substituted by halogen or alkoxy having 1 to 4 carbon atoms or represents cycloalkyl having 3 to 8 carbon atoms which is optionally substituted by halogen, alkyl or alkoxy having in each case 1 to 4 carbon atoms,
- G represents a single bond, methanediyl, 1,1-ethanediyl, 1,2-ethanediyl, 1,1-, 1,2-, 1,3- or 2,2-propanediyl, 1,1-, 1,2-, 1,3-, 1,4-, 2,2-, 2,3-butanediyl or 1,1-, 1,2- or 1,3-(2-methyl-propanediyl), —O—CH₂— (where Z is attached to the oxygen atom),
- Z
  - represents methyl, ethyl, n- or i-propyl, n-, i-, s- or t-butyl, each of which is optionally mono- to trisubstituted by identical or different substituents selected from the group consisting of chlorine fluorine, bromine, cyano, hydroxyl, amino, methoxy, ethoxy, methylthio, ethylthio, methylsulphinyl, ethylsulphinyl, methylsulphonyl, ethylsulphonyl, difluoromethoxy, trifluoromethoxy, difluorochloromethoxy, trifluoroethoxy, difluoromethylthio, trifluoromethylthio, difluorochloromethylthio, trifluoromethyl-sulphinyl or trifluoromethylsulphonyl;
  - represents phenyl, cyclopropyl, cyclobutyl, cyclopentyl, cylohexyl, cycloheptyl, oxazolyl, benzofuranyl, 1,2,4-thiadiazolyl, 1,3,4-thiadiazolyl, 1,2,4-oxadiazolyl, 1,3,4-oxadiazolyl, pyridinyl, pyrimidyl, pyridazinyl, pyrazinyl, 1,2,3-triazinyl, 1,2,4-triazinyl, 1,3,5-triazinyl or 5,6-dihydro-1,4,2-dioxazinyl, each of which is optionally mono- to trisubstituted by identical or different substituents, where the possible substituents are preferably selected from the list below:
    - fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxy-carbonyl, ethoxycarbonyl,
  - in each case doubly attached methylenedioxy, ethylenedioxy, each of which is optionally mono- to tetrasubstituted by identical or different substituents selected from the group consisting of fluorine, chlorine, methyl, trifluoromethyl and ethyl or a grouping,

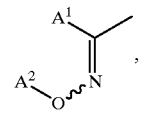

where
- A¹ represents methyl, ethyl, n- or i-propyl, n-, i-, s- or t-butyl, cyclopropyl or cyclobutyl and
- A² represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl and
- E¹, E², E³ and E⁴ are identical or different and, independently of one another each represents hydrogen, alkyl or hydroxyalkyl having in each case 1 to 4 carbon atoms or halogenoalkyl having 1 to 4 carbon atoms and 1 to five identical or different halogen atoms, or
- E¹ and E² or E¹ and E³ or E³ and E⁴ together with the respective carbon atoms to which they are attached form a cycloaliphatic ring having five, six or seven carbon atoms and
- L¹, L², L³ and L⁴ are identical or different and, independently of one another, each represents hydrogen, halogen, cyano, nitro, represents alkyl, alkoxy, alkylthio, alkylsulphinyl or alkylsulphonyl having in each case 1 to 6 carbon atoms and being in each case optionally substituted by 1 to 5 halogen atoms.

2. Compounds of the formula (I) according to claim 1 in which
- R¹ represents hydrogen, cyano, methyl, ethyl, n- or i-propyl, n-, i-, s- or t-butyl, trifluoromethyl, trifluoroethyl, cyclopropyl, cyclobutyl,
- R² represents hydrogen, methyl, ethyl, n- or i-propyl, n-, i-, s- or t-butyl, trifluoromethyl, trifluoroethyl, cyclopropyl, cyclobutyl,
- G represents a single bond, methanediyl, 1,1-ethanediyl, 1,2-ethanediyl, 1,1-, 1,2-, 1,3- or 2,2-propanediyl, 1,1-, 1,2-, 1,3-, 1,4-, 2,2-, 2,3-butanediyl or 1,1-, 1,2- or 1,3-(2-methyl-propanediyl), —O—CH₂— (where Z is attached to the oxygen atom),
- Z represents methyl, ethyl, n- or i-propyl, n-, i-, s- or t-butyl, each of which is optionally mono- to trisubstituted by identical or different substituents selected from the group consisting of chlorine fluorine, bromine, cyano, hydroxyl, amino, methoxy, ethoxy, methylthio, ethylthio, methylsulphinyl, ethylsulphinyl, methylsulphonyl, ethylsulphonyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl;

represents phenyl, cyclopropyl, cyclobutyl, cyclopentyl, cylohexyl, cycloheptyl, oxazolyl, benzofuranyl, 1,2,4-thiadiazolyl, 1,3,4-thiadiazolyl, 1,2,4-oxadiazolyl, 1,3,4-oxadiazolyl, pyridinyl, pyrimidyl, pyridazinyl, pyrazinyl, 1,2,3-triazinyl, 1,2,4-triazinyl, 1,3,5-triazinyl or 5,6-dihydro-1,4,2-dioxazinyl, each of which is optionally mono- to trisubstituted by identical or different substituents, where the possible substituents are preferably selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, in each case doubly attached methylenedioxy, ethylenedioxy, each of which is optionally mono- to tetrasubstituted by identical or different substituents selected from the group consisting of fluorine, chlorine, methyl, trifluoromethyl and ethyl or a grouping

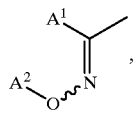

where
A$^1$ represents methyl, ethyl, n- or i-propyl, n-, i-, s- or t-butyl, cyclopropyl or cyclobutyl and
A$^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl and E$^1$, E$^2$, E$^3$ and E$^4$ are identical or different and, independently of one another, each represents hydrogen, methyl, ethyl, n- or i-propyl, n-, i-, s- or t-butyl, hydroxymethyl, trifluoromethyl or trifluoroethyl, or E$^1$ and E$^2$ or E$^1$ and E$^3$ or E$^3$ and E$^4$ together with the respective carbon atoms to which they are attached form a cycloaliphatic ring having five, six or seven carbon atoms and L$^1$, L$^2$, L$^3$ and L$^4$ are identical or different and, independently of one another, each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphonyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

3. Compounds of the formula (I) according to claim 1, in which

R$^1$ represents methyl or cyclopropyl,
R$^2$ represents hydrogen,
G represents a single bond or —O—CH$_2$— (where Z is attached to the oxygen atom),
Z represents methyl, ethyl, n- or i-propyl, n-, i-, s- or t-butyl, each of which is optionally mono- to trisubstituted by identical or different constituents selected from the group consisting of chlorine fluorine, bromine, cyano, hydroxyl, amino, methoxy, ethoxy, methylthio, ethylthio, methylsulphinyl, ethylsulphinyl, methylsulphonyl, ethylsulphonyl, difluoromethoxy, trifluoromethoxy, difluorochloromethoxy, trifluoroethoxy, difluoromethylthio, trifluoromethylthio, difluorochloromethylthio, trifluoromethylsulphinyl and trifluoromethylsulphonyl;

represents phenyl, 1,2-oxazolyl or benzofuranyl which is optionally mono- to trisubstituted by identical or different substituents, where the possible substituents are preferably selected from the list below:
fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, in each case doubly attached methylenedioxy, ethylenedioxy, each of which is optionally mono- to tetrasubstituted by identical or different substituents selected from the group consisting of fluorine, chlorine, methyl, trifluoromethyl and ethyl or a grouping,

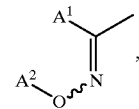

where
A$^1$ represents methyl, ethyl, n- or i-propyl, n-, i-, s- or t-butyl, cyclopropyl or cyclobutyl and
A$^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl, E$^1$ and E$^2$ are identical or different and, independently of one another, each represents hydrogen or methyl,
E$^3$ and E$^4$ each represent hydrogen,
L$^1$ and L$^3$ are identical or different and, independently of one another, each represents hydrogen or methyl and
L$^2$ and L$^4$ each represent hydrogen.

4. A pesticide composition comprising at least one compound of the formula (I) according to claim 1 and an extender and/or surfactant.

5. A method for controlling pests comprising applying compounds of the formula (I) according to claim 1 on pests and/or their habitat.

6. A process for preparing compounds of the formula (I) as defined in claim 1 comprising reacting 3-(1-hydroxy-phenyl-1-alkoximinomethyl)dioxazines of the general formula

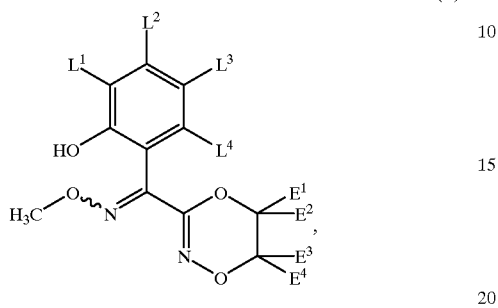

(II)

wherein
$E^1$, $E^2$, $E^3$, $E^4$, $L^1$, $L^2$, $L^3$, and $L^4$ are each as defined in claim 2 with an acrylic acid halide of the general formula (III)

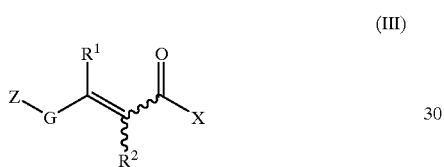

(III)

wherein
G, $R^1$, $R^2$ and Z are each as defined in claim 2 and X represents a halogen.

7. The process of claim 6 wherein the reaction is carried out in the presence of a diluent and/or an acid acceptor.

8. Compounds according to claim 1, wherein $E^1$, $E^2$, $E^3$ and $E^4$ are identical or different and, independently of one another each represents hydrogen, alkyl or hydroxyalkyl having in each case 1 to 4 carbon atoms or halogenoalkyl having 1 to 4 carbon atoms and 1 to five identical or different halogen atoms.

9. Compounds according to claim 1, wherein $L^1$, $L^2$, $L^3$ and $L^4$ are identical or different and, independently of one another, each represents hydrogen or halogen, or represents alkyl or alkoxy having in each case 1 to 6 carbon atoms and being in each case optionally substituted by 1 to 5 halogen atoms.

10. Compounds of the formula (I)

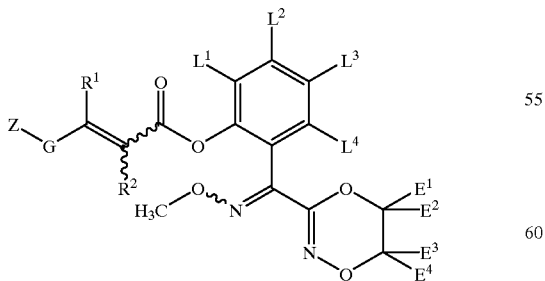

in which
$R^1$ represents hydrogen, cyano, methyl, ethyl, n- or i-propyl, n-, i-, s- or t-butyl, trifluoromethyl, trifluoroethyl, cyclopropyl, cyclobutyl, $R^2$ represents hydrogen, methyl, ethyl, n- or i-propyl, n-, i-, s- or t-butyl, trifluoromethyl, trifluoroethyl, cyclopropyl, cyclobutyl, G represents a grouping

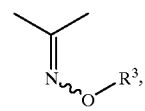

in which
$R^3$
represents hydrogen or represents methyl, ethyl, n- or i-propyl, n-, -1-, s- or t-butyl, each of which is optionally mono- to trisubstituted by fluorine, chlorine, bromine, methoxy, ethoxy, (each of which is optionally substituted by fluorine and/or chlorine),
represents allyl, crotonyl, 1-methyl-allyl, propargyl or 1-methyl-propargyl, each of which is optionally mono- to trisubstituted by fluorine or chlorine;
represents cyclopropyl, cyclobutyl, cyclopentyl or cyclohexyl, each of which is optionally mono- to hexasubstituted by fluorine, chlorine, bromine, methoxy, ethoxy, phenyl (which is optionally substituted by fluorine, chlorine, bromine, cyano, methyl, ethyl, n- or i-propyl, n-, i-, s- or t-butyl, trifluoromethyl, methoxy, ethoxy, n- or i-propoxy, difluoromethoxy or trifluoromethoxy), methyl, ethyl, n- or i-propyl;
represents benzyl, phenyl-1-ethyl or phenyl-2-ethyl, each of which is optionally mono- to trisubstituted in the phenyl moiety, where the possible substituents are preferably selected from the list below:
Fluorine, chlorine, bromine, cyano, nitro, methyl, ethyl, n- or i-propyl, n-, i- s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorohloromethoxy, trifluoroethoxy, difluoromethylthio, difluorochloromethylthio, trifluoromethylthio, trifluoromethylsulphinyl, trifluoromethylsulphonyl, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl;
in each case doubly attached trimethylene (propane-1,3-diyl), methylenedioxy or ethylenedioxy, each of which is optionally mono- or polysubstituted by
identical or different substituents selected from the group consisting of fluorine, chlorine, methyl, trifluoromethyl, ethyl, n- or i-propyl,
Z
represents methyl, ethyl, n- or i-propyl, n-, i-, s- or t-butyl, each of which is optionally mono- to trisubstituted by identical or different substituents selected from the group consisting of chlorine fluorine, bromine, cyano, hydroxyl, amino, methoxy, ethoxy, methylthio, ethylthio, methylsulphinyl, ethylsulphinyl, methylsulphonyl, ethylsulphonyl, difluoromethoxy, trifluoromethoxy, difluorochloromethoxy, trifluoroethoxy, difluoromethylthio, trifluoromethylthio, difluorchloromethylthio, trifluoromethylsulphinyl or trifluoromethylsulphonyl;

represents vinyl, allyl or propargyl, each of which is optionally mono- to trisubstituted by identical or different substituents selected from the group consisting of chlorine fluorine or bromine; or represents phenyl, cyclopropyl, cyclobutyl, cyclopentyl, cyclohexyl, cycloheptyl, 1,2-oxazolyl, benzofuranyl, 1,2,4-thiadiazolyl, 1,3,4-thiadiazolyl, 1,2,4-oxadiazolyl, 1,3,4-oxadiazolyl, pyridinyl, pyrimidyl, pyridazinyl, pyrazinyl, 1,2,3-triazinyl, 1,2,4-triazinyl, 1,3,5-triazinyl or 5,6-dihydro-1,4,2-dioxazinyl, each of which is optionally mono- to trisubstituted by identical or different substituents, where the possible substituents are preferably selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, in each case doubly attached methylenedioxy, ethylenedioxy, each of which is optionally mono- to tetrasubstituted by identical or different substituents selected from the group consisting of fluorine, chlorine, methyl, trifluoromethyl or ethyl or a grouping

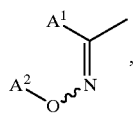

where
A¹ represents methyl, ethyl, n- or i-propyl, n-, i-, s- or t-butyl, cyclopropyl or cyclobutyl and
A² represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl and $E^1$, $E^2$, $E^3$ and $E^4$ are identical or different and, independently of one another, each represents hydrogen, methyl, ethyl, n- or i-propyl, n-, i-, s- or t-butyl, hydroxymethyl, trifluoromethyl or trifluoroethyl, or $E^1$ and $E^2$ or $E^1$ and $E^3$ or $E^3$ and $E^4$ together with the respective carbon atoms to which they are attached form a cycloaliphatic ring having five, six or seven carbon atoms and $L^1$, $L^2$, $L^3$ and $L^4$ are identical or different and, independently of one another, each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

11. Compounds of the formula (I)

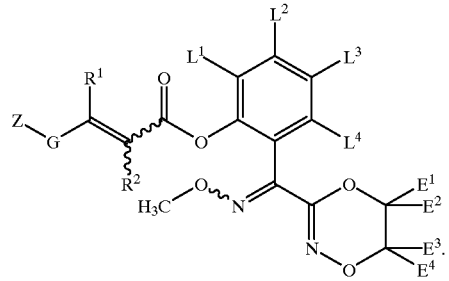

in which
$R^1$ represents methyl or cyclopropyl,
$R^2$ represents hydrogen,
G represents a grouping

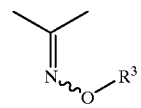

in which
$R^3$ represents methyl or represents benzyl which is optionally mono- to trisubstituted in the phenyl moiety by fluorine, chlorine, bromine, cyano, nitro, methyl or methoxy, Z
represents methyl, ethyl, n- or i-propyl, n-, i-, s- or t-butyl, trifluoromethyl, trifluoroethyl, methoxymethyl, methylthiomethyl or methylsulphonylmethyl, vinyl, dichlorovinyl, allyl, propargyl, cyclopropyl, methylcyclopropyl, cyclobutyl, cyclopentyl, cylohexyl or represents 1,2-oxazolyl, benzofuranyl or, in particular, phenyl each of which is optionally mono- to trisubstituted by identical or different substituents, where the possible substituents are preferably selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethyisulphinyl or trifluoromethylsulphonyl, methoxycarbonyl, ethoxycarbonyl, in each case doubly attached methylenedioxy, ethylenedioxy, each of which is optionally mono- to tetrasubstituted by identical or different substituents selected from the group consisting of fluorine, chlorine, methyl, trifluoromethyl and ethyl or a grouping,

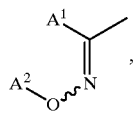

where
A¹ represents methyl, ethyl, n- or i-propyl, n-, i-, s- or t-butyl, cyclopropyl or cyclobutyl and
A² represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl, $E^1$ and $E^2$ are identical or different and, independently of one another, each represents hydrogen or methyl, $E^3$ and $E^4$ each represent hydrogen, $L^1$ and $L^3$ are identical or different and, independently of one another, each represents hydrogen or methyl and $L^2$ and $L^4$ each represent hydrogen.

12. A pesticide composition comprising at least one compound of the formula (I) according to claim 11 and an extender and/or surfactant.

13. A method for controlling pests comprising applying compounds of the formula (I) according to claim 11 on pests and/or their habitat.

14. A process for preparing compounds of the formula (I) as defined in claim 11 comprising reacting 3-(1-hydroxy-phenyl-1-alkoximinomethyl)dioxazines of the general formula

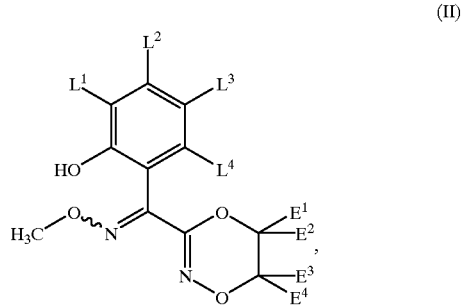

wherein
$E^1$, $E^2$, $E^3$, $E^4$, $L^1$, $L^2$, $L^3$, and $L^4$ are each as defined in claim 6 with an acrylic acid halide of the general formula (III)

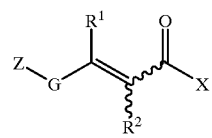

wherein
G, $R^1$, $R^2$ and Z are each as defined in claim 11 and X represents a halogen.

15. The process of claim 14 wherein the reaction is carried out in the presence of a diluent and/or an acid acceptor.

* * * * *